(12) United States Patent
Keränen et al.

(10) Patent No.: US 10,856,983 B2
(45) Date of Patent: Dec. 8, 2020

(54) SYSTEM FOR CARDIAC VALVE REPAIR

(71) Applicant: Medtentia International Ltd Oy, Helsinki (FI)

(72) Inventors: Olli Keränen, Bjärred (SE); Jani Virtanen, Sipoo (FI); Mark Pugh, Coolaney (IE); Ger O'Carroll, County Sligo (IE); Adrian Moran, County Sligo (IE)

(73) Assignee: MEDTENTIA INTERNATIONAL LTD. OY, Helsinki (FI)

( * ) Notice: Subject to any disclaimer, the term of this patent is extended or adjusted under 35 U.S.C. 154(b) by 0 days.

(21) Appl. No.: 14/762,401

(22) PCT Filed: Jan. 27, 2014

(86) PCT No.: PCT/EP2014/051544
§ 371 (c)(1),
(2) Date: Jul. 21, 2015

(87) PCT Pub. No.: WO2014/114798
PCT Pub. Date: Jul. 31, 2014

(65) Prior Publication Data
US 2015/0351908 A1    Dec. 10, 2015

Related U.S. Application Data

(60) Provisional application No. 61/756,670, filed on Jan. 25, 2013, provisional application No. 61/756,633, (Continued)

(30) Foreign Application Priority Data

Jan. 25, 2013  (EP) .................................... 13152768
Jan. 25, 2013  (EP) .................................... 13152769

(Continued)

(51) Int. Cl.
  *A61F 2/24*    (2006.01)
  *A61M 25/00*   (2006.01)
  (Continued)

(52) U.S. Cl.
  CPC ............ *A61F 2/2445* (2013.01); *A61F 2/246* (2013.01); *A61F 2/2463* (2013.01);
  (Continued)

(58) Field of Classification Search
  CPC .... A61F 2/2442; A61F 2/2445; A61F 2/2466; A61F 2/2496; A61F 2/2463
  See application file for complete search history.

(56) References Cited

U.S. PATENT DOCUMENTS 6,355,030 B1 * 3/2002  Aldrich et al. ....... A61F 2/2427
                                                      606/28
2006/0259137 A1   11/2006  Artof et al.
(Continued)

FOREIGN PATENT DOCUMENTS

WO    WO2005/039428 A2    5/2005

OTHER PUBLICATIONS

WIPO, International Preliminary Examining Authority (European Patent Office), International Preliminary Report on Patentability dated May 19, 2015 in International Patent Application No. PCT/EP2014/051544, 16 pages.
(Continued)

*Primary Examiner* — Suba Ganesan
(74) *Attorney, Agent, or Firm* — Patent Grove, LLC; Tomas Friend

(57) ABSTRACT

A medical system for repairing a mitral valve comprising a catheter (5) with a temporary valve (10), a commissure
(Continued)

locator device (20), wherein the commissure locator device and the temporary valve are connected, and an annuloplasty implant (30).

10 Claims, 5 Drawing Sheets

Related U.S. Application Data filed on Jan. 25, 2013, provisional application No. 61/756,649, filed on Jan. 25, 2013, provisional application No. 61/756,657, filed on Jan. 25, 2013, provisional application No. 61/756,663, filed on Jan. 25, 2013.

(30) Foreign Application Priority Data

| Jan. 25, 2013 | (EP) | 13152770 |
| Jan. 25, 2013 | (EP) | 13152771 |
| Jan. 25, 2013 | (EP) | 13152774 |

(51) Int. Cl.
*A61M 25/02* (2006.01)
*A61B 17/00* (2006.01)

(52) U.S. Cl.
CPC ....... *A61F 2/2466* (2013.01); *A61M 25/0075* (2013.01); *A61B 2017/00783* (2013.01); *A61F 2/2454* (2013.01); *A61F 2/2457* (2013.01); *A61F 2230/0069* (2013.01); *A61F 2250/0059* (2013.01); *A61M 2025/0293* (2013.01)

(56) References Cited

U.S. PATENT DOCUMENTS

| 2007/0038293 | A1* | 2/2007 | St. Goar et al. | A61F 2/2445 623/2.11 |
| 2010/0331971 | A1* | 12/2010 | Keranen | A61F 2/2445 623/2.11 |
| 2012/0271411 | A1 | 10/2012 | Duhay et al. | |

OTHER PUBLICATIONS

WIPO, European International Search Authority, International Search Report dated May 21, 2015 in International Patent Application No. PCT/EP2014/051544, 6 pages.

\* cited by examiner

SYSTEM FOR CARDIAC VALVE REPAIR

RELATED APPLICATIONS

This application is the U.S. National Phase of and claims priority to International Patent Application No. PCT/EP2014/051544, International Filing Date Jan. 27, 2014, entitled A System For Cardiac Valve Repair, which claims benefit of European Application No. EP13152768.1, filed Jan. 25, 2013 entitled A System For Cardiac Valve Repair; U.S. Provisional Application Ser. No. 61/756,670, filed Jan. 25, 2013 entitled A System For Cardiac Valve Repair; U.S. Provisional Application Ser. No. 61/756,633, filed Jan. 25, 2013 entitled A Medical Device And Method For Facilitating Selection Of An Annuloplasty Implant; European Application No. EP13152774.9, filed Jan. 25, 2013 entitled A Medical Device And Method For Facilitating Selection Of An Annuloplasty Implant; European Application No. EP13152770.7, filed Jan. 25, 2013 entitled A Valve For Short Time Replacement For Taking Over The Function Of, And/Or For Temporary Or Partial Support Of, A Native Valve In A Heart; U.S. Provisional Application Ser. No. 61/756,649, filed Jan. 25, 2013 entitled A Valve For Short Time Replacement, For Taking Over The Function Of And/Or For Temporary Or Partial Support Of A Native Valve In A Heart And A Method Of Delivery Therefor; European Application No. EP13152769.9, filed Jan. 25, 2013 entitled A Medical System, And A Device For Collecting Chordae And/Or Leaflets; U.S. Provisional Application Ser. No. 61/756,657, filed Jan. 25, 2013 entitled A Medical System, And A Device For Collecting Chordae And/Or Leaflets And A Method Therefor; European Application No. EP13152771.5, filed Jan. 25, 2013 entitled Temporary Atrium Support Device; and U.S. Provisional Application Ser. No. 61/756,663, filed Jan. 25, 2013 entitled Temporary Atrium Support Device; all of which are incorporated herein by reference in their entireties.

BACKGROUND OF THE INVENTION

1. Field of the Invention

This invention pertains in general to the field of cardiac valve repair. More particularly the invention relates to mitral valve repair.

2. Description of the Prior Art

It is known that cardiac valve repair is a time critical and difficult procedure. Known systems and methods of today takes long time to perform and are highly advanced for medical staff to perform. Thus the life of a patient depends very much on the skill of the medical staff and on the time of discovery of the problem associated with the cardiac valve.

Thus, there is a need for a new system and method for performing a cardiac valve repair in an easier and faster way. Hence, an improved system and method for cardiac valve repair would be advantageous.

SUMMARY OF THE INVENTION

Accordingly, examples of the present invention preferably seek to mitigate, alleviate or eliminate one or more deficiencies, disadvantages or issues in the art, such as the above-identified, singly or in any combination by providing a system and a method that repairs a cardiac valve, according to the appended patent claims.

According to aspects of the invention, a system and method for cardiac valve repair are disclosed.

According to a first aspect of the invention, a system is provided, the medical system for repairing a mitral valve comprises a temporary valve, a commissure locator device, wherein the commissure locator device and the temporary valve are connected, and an annuloplasty implant.

According to a second aspect of the invention, a method for repairing a mitral valve is provided, comprising the steps of, in one manoeuvre, positioning a temporary valve by use of a commissure locator device connected to the temporary valve and measuring a size and/or a shape of an annuloplasty implant by use of the commissure locator device, positioning the annuloplasty implant at the mitral valve, and securing the annuloplasty implant at the mitral valve for repairing the mitral valve.

Further examples of the invention are defined in the dependent claims, wherein features for the second and subsequent aspects of the invention are as for the first aspect mutatis mutandis.

Some examples of the invention provide for in one maneuver position and decide a shape and/or size of an annuloplasty implant.

Some examples of the invention also provide for medical staff in a quick and easy way maintain heart function when deploying an annuloplasty implant.

Some examples of the invention also provide for quickly repairing a problem with a mitral valve or temporary stabilize a patient so a decision on how to continue can be made without stress.

Some examples of the invention also provide for easy orientation of a commissure locator device and a temporary valve.

Some examples of the invention also provide for blood to be collected and guided to a temporary valve for a more secure and reliable flow of blood from a ventricle to an atrium and/or vice versa.

Some examples of the invention also provide for a very stable construction.

Some examples of the invention also provide for further securing a commissure locator device and a temporary valve in a direction of blood flow to and from an atrium.

Some examples of the invention also provide for an easier way for a surgeon to position and secure an annuloplasty implant since more space is created in an atrium giving the surgeon more freedom to orientate the annuloplasty implant.

Some examples of the invention also provide for a further securing at a mitral valve.

Some examples of the invention also provide for quickly and easily repair a valve defect, such as regurgitation in a patient.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the invention are capable of will be apparent and elucidated from the following description of examples of the present invention, reference being made to the accompanying drawings, in which.

DESCRIPTION OF THE PREFERRED EXAMPLES

Figure 1:
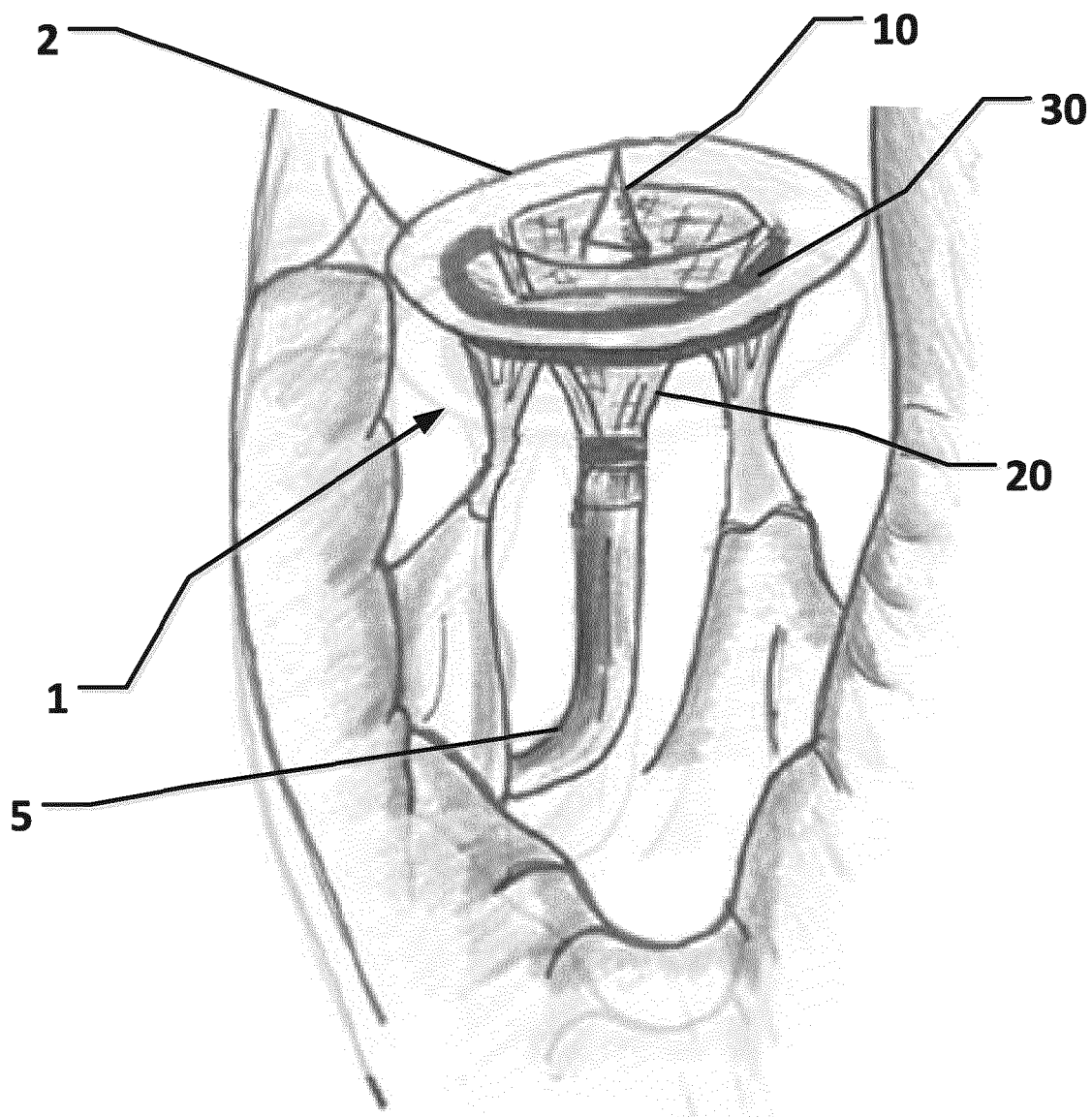
FIG. 1 is a side view of a medical system 1 for repairing a mitral valve.

Specific examples of the invention now will be described with reference to the accompanying drawings. This invention may, however, be embodied in many different forms and should not be construed as limited to the examples set forth herein; rather, these examples are provided so that this disclosure will be thorough and complete, and will fully convey the scope of the invention to those skilled in the art. The terminology used in the detailed description of the examples illustrated in the accompanying drawings is not intended to be limiting of the invention. In the drawings, like numbers refer to like elements.

The following description focuses on an example of the present invention applicable to a method for mitral valve repair. However, it will be appreciated that the invention is not limited to this application but may be applied to many other types of valve repairs including for example an aortic valve repair.

In an example of the invention illustrated in FIG. 1, a medical system 1 for repairing a mitral valve 2 comprising a temporary valve 10, a commissure locator device 20, wherein the commissure locator device 20 and the temporary valve 10 are connected, and an annuloplasty implant 30. By using the medical system 1 described above a minimum of devices 10, 20 and 30 need to be used so that a surgeon or similar medical staff can in a quick and easy way maintain heart function when deploying the annuloplasty implant 30 and select the proper size and/or shape of the annuloplasty implant 30. This allows for quickly repairing a problem with the mitral valve 2 or temporary stabilise the patient so a decision on how to continue can be made without the stress of having an instable patient due to valve problems.

Also illustrated in FIG. 1, is a deployment catheter 5 which in this example is a delivery device for all implements 10, 20 and 30 used in the medical system 1. In another example the deployment catheter 5 is a part of the delivery device. Thus, the delivery catheter 5 may be utilized for delivery of a commissure locator device 20, a temporary valve 10 and/or an annuloplasty implant 30. Additionally the delivery catheter 5 is capable of being rotated, angled and/or otherwise steered at and to the mitral valve 2 from a desired position in or outside the body by the surgeon. Such access to the mitral valve 2 is in one example performed transfemoral and in another example performed transapical.

Figure 2:
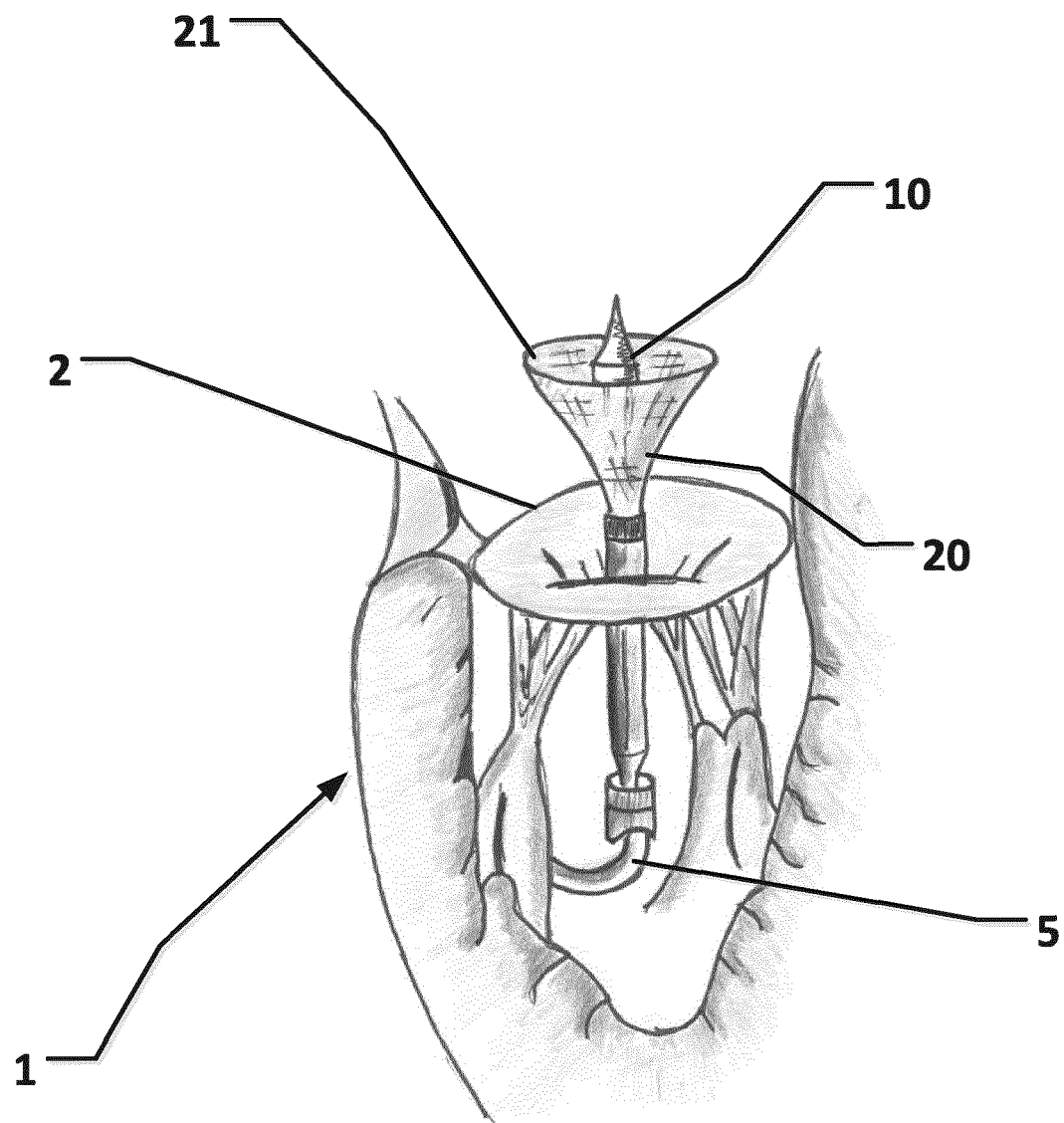
FIG. 2 is a side view of a medical system 1 for repairing a mitral valve.

In an example the commissure locator device 20 comprises a catheter 5 with a proximal end and a distal end, such as the deployment catheter 5. The commissure locator device 20 further comprises an extension member 21, as illustrated in FIG. 2, at least partly arranged inside the catheter 5 with an operator end and a measurement end. The measurement end of the extension member 21 is extendable relative from the distal end of the catheter 5 for apposition with at least one commissure of a cardiac valve, such as the mitral valve 2. A measure related to the selection of the annuloplasty implants 30 shape and/or size is based on at least an extended length of the measurement end of the extension member 21 from the distal end of the catheter 5, positioned at the cardiac valve, to the at least one commissure. By using the commissure locator device 20 providing the measure related to the selection of the shape and/or size of the annuloplasty implant 30 the operator of the commissure locator device 20 is facilitated to in an easy and reliable way select the shape and/or size of the annuloplasty implant 30.

In an example the commissure locator device 20 comprises extension member 21 having an oval cone shape. By using the commissure locator device 20 having the oval cone shaped extension member 21, the commissure locator device 20 is in contact with most or all of the tissue of the valves. This contact allows for easy orientation of the commissure locator device and the temporary valve 10. Further, the oval cone shaped extension member 21 allows for blood to be collected and guided by the cone shape to the temporary valve 10 for a more secure and reliable flow of blood from a ventricle to the atrium and/or vice versa. Hence, there will be less leakage with the commissure locator device 20 than other types. The oval cone shaped member is in an example formed of at least one extending sheet. In another example the oval cone shaped member is formed from several braided, extending and/or interwoven shape members.

In another example the extension member 21 is a rod or alternatively a pole and/or other long thin member with a cylindrical, circular, squared or rectangular base, capable of being arranged in the catheter 5. In an example the extension member 21 is a rod extended perpendicular from the catheter 5 outwards towards the at least one commissure. In another example the extension member 21 is of a semi-circular shape such as a leaf shaped and where the semi-circular shape is directed towards the at least one commissure and has a spring action for apposition at at least one commissure.

In another example the extension member 21 is rotationally arranged in the catheter 5 for apposition with the at least one commissure. In another example the extension member 21 is slidably arranged in the catheter 5. These arrangements allow for easy use and movement of the extension member 21 and the catheter 5. Alternatively, the arrangement allows for easy use and movement independently of each other.

The extension member 21 is made of a suitable material compatible with and for use in the catheter 5 and in a heart, such as of titanium, nitinol, polymer, carbon fiber, textiles, all in solid forms or in braided or sandwich structure forms. The extension member 21 has a length that is at least as long as the catheter 5 and a distance from the catheter 5 to the at least one commissure. The extension member 21 is preferably long enough to be operated at the operator end by the proximal end of the catheter 5 and still extendable at the measurement end at the distal end of the catheter 5, i.e. the extension member 21 extends out of and from the catheter 5 at both ends of the catheter 5 when used by the operator.

In another example of the extension member 21 the extension member 21 has a length wherein the measurement end of the extension member 21 only extends out and from the distal end of the catheter 5 and the operator end of the extension member 21 is arranged at level with the proximal end of the catheter 5, i.e. the extension member 21 only extends from the catheter 5 at the distal end of the catheter 5 when used by the operator. By using the maneuverable extension member 21 the operator measures a distance from the catheter 5 at the cardiac valve to the at least one commissure and bases the size and/or shape of the annuloplasty implant 30 on the distance.

The extension member 21 comprises in one example the measure related to the annuloplasty implants 30 shape and/or size indicated at the operator end of the extension member 21. By having the operator end of the extension member 21 indicating the measure related to the size and/or shape of the annuloplasty implant 30, the operator can quickly and with ease visually see which annuloplasty implant 30 the operator should choose.

In another example the extension member 21 comprises two sections separable towards each of the mitral valve 2's commissures. By using two sections that are separable towards two commissures at the mitral valve 2 a distance between the two commissures is measured immediately and faster than when using the extension member 21 without the two separable sections.

In other example the two separable sections are upon extension from the catheter 5 aligned in a plane extending along a direction of the proximal end of the catheter 5. By having the two separable sections aligned and extended in the plane parallel to the direction of the catheter 5 the two sections will be easier to control due to their shared alignment with the direction of the catheter 5.

In yet another example the two separable sections separate with an opposite inclined separation angle. By having the two sections separate with opposite inclined angle of separation the two separable sections extend the same distance outwards towards the commissures and thus are easier to apposition with the two commissures due to their synchronised extension.

The two separable sections are in one example an integral continuation of the extension member 21. By having the two separable sections being the integral continuation of the extension member 21 the two separable sections better responds to maneuvers, such as rotation and/or extension of the extension member 21 performed by the operator. Additionally, a requirement for manufacturing of the extension member 21 is greatly reduced since the extension member 21 and the two separable extensions are made in one piece. In one example the two separable sections' and the extension member 21's mechanical aspects such as increased breaking resistance and/or improved rotational force, are greatly improved because the extension member 21 and the two separable sections are sized and/or shaped dependent on each other.

Alternatively, the two separable sections are joined to the measurement end of the extension member 21. By allowing the two separable sections to be joined at the measurement end of the extension member 21 they may be manufactured from a different material than the extension member 21 and thus have other material properties with respect to bending, rotation and/or biocompatibility.

In another example, the extension member 21 comprises two separable sections which further comprises a c-shaped or claw shaped end. This claw shaped end is large enough to encompass an edge of a valve leaflet when aligned at the at least one commissure so that the extension member 21 is further secured at the at least one commissure.

In one example the commissure locator device 20 further comprises a force detection unit connected to the extension member 21 for detection of a manoeuvre force applied to the extension member 21. By using the force detection unit for detecting the manoeuvre force applied to the extension member 21 it is possible to get a further more reliable indication of when the extension member 21 is at apposition or in contact too or with at least one commissure.

In a further example of the extension member 21, the measurement end of the extension member 21 comprises anchoring means for attaching anchors at at least one commissure for the annuloplasty implant 30. Alternatively, one anchor is attached at one commissure. By having the extension member 21 comprising anchoring means for attaching anchors for the annuloplasty implant 30 it is possible to detect the location of the at least one commissure and following the localization attach anchors at the commissure so that the annuloplasty implant 30 can be anchored. This allows for fast deployment of the annuloplasty implant 30 after the at least one commissure is found and the size and/or shape of the annuloplasty implant 30 has been chosen. In an example the anchoring means is a claw or similar that allows for gripping the anchors.

In one example, the anchors comprise at least one guiding unit or ring. By using at least one guiding unit or rings as anchors the annuloplasty implant 30, which preferably has the shape of a helix ring, is rotated into place at the cardiac valve by use of the anchors. For example, when using rings as anchors the annuloplasty implant 30 is inserted through and slides in the rings securing the annuloplasty implant 30 at the commissures. In an example the anchors are arranged in the atrium and catch and guides an upper part of the helix ring. In another example the anchors are arranged in the ventricle and catch and guides a lower part of the helix ring. In yet another example the anchors are arranged in both the atrium and the ventricle and catch both parts of the helix ring and part of the annulus. This allows for the helix ring to be anchored in different ways from different entering points at the commissure and provides for stabilizing the helix ring at suitable locations.

As discussed above, in one example the anchoring means comprises anchors that are used as guides, i.e. guiding means, for the annuloplasty implant at the at least one commissure, and i. In another example the anchors are used alternatively and/or in addition, as means for guiding the annuloplasty implant at the at least one commissure before the anchors may be attached at the at least one commissure. This allows the user to both measure the correct size of the annuloplasty implant and guide the annuloplasty implant into place in an easy way without removing the medical device 1 when placed at the at least one commissure and at the same time avoid attaching the anchors at the at least one commissure, thus reducing the time for deploying the annuloplasty implant in the patient. In this example, the means for guiding is preferably may be generally open or c-shaped which allows the annuloplasy implant to be guided into place in the heart without attaching the means for guiding at the at least one commissure and which allows for removal of the means for guiding, after the annuloplasty implant is implanted in the patient, through the opening of the c-shape. FIG. 8b shows the extension member comprising guiding means that are generally open or C-shaped for guiding an implant into place. Other shapes that can be used are substantially loop-shaped, triangle-shaped, ring-shaped, or any other suitable shape that allows for guiding the annuloplasty implant into place and/or allows for removing the means for guiding when the annuloplasty implant is implanted in the heart. The extension member may have guiding means at each the two lateral parts of the extension member that are to be placed at the commissures.

In a further example of the extension member 21, the measurement end of the extension member 21 is shaped and/or formed as one coherent member. The extension member 21 may thus be formed as a continuous single or one-piece loop, i.e. a closed design. By using the extension member 21 formed from one piece closed design the member is much more stable in its construction and easier to manoeuvre in the heart. Further, the continuous loop provides for particularly efficient stabilization of the anatomy and improving the precision by which the implant can be placed at the valve. Further, the continuous loop minimizes undesired interference with the chordae in the heart that would otherwise be the risk when having projections, edges, kinks etc. The extension member may comprise a continuous loop having a distal portion being curved outwardly in a direction from the distal end of the catheter. Such curved shape further reduces the risk of damaging any chordae due the smooth shape. In an example the distal portion bridges the two guiding means on the extension member. This provides for an atraumatic extension member that effectively stabilizes the valve, while at the same time providing guiding means for the implant. The principle of use and mode of use is the same as for the other examples of extension members described in this application. Hence, the measurement, expansion, material and so on are the same and operates in the same way.

In another example, the extension member 21 comprises a leaflet limiter. The leaflet limiter is not limited to be used only with the coherent extension member 21 but the other types of extension members disclosed in this application may also have the leaflet limiter. The leaflet limiter limits abnormal movement, such as prolapse, of the leaflets into the atrium. Such abnormal movement may arise if a chordae, or several chordae, that usually limits the movement of the leaflet is completely destroyed and the leaflet may thus freely move in the left atrium and/or left chamber. The leaflet limiter is made of a material that expands with the extension member 21, and/or and it is may be made of the same material as the extension member 21. The leaflet limiter may also be such that it can be bent, twisted or otherwise collapsed into the catheter 5 and then assume a desired shape when released from the catheter 5. Alternatively, the leaflet limiter is expanded by a spring back motion and/or force when exited from the catheter 5 with the extension member 21. An example of the leaflet limiter, is a crossbar that extends between two anchoring points of the extension member 21 and is projected laterally from an intersecting plane of the anchoring points of the extension member 21. The leaflet limiter may be of one piece or be made up of several pieces and/or have a number of different shapes and/or have various placements. One example of a shape that limits but not damage the leaflet(s) when hindering the movement into the atrium would be to have a simple straight projection outwards towards the leaflets from the extension member 21 with a blunt end, which can limit the movement but not damage the leaflet(s) when hindering the movement into the atrium. Preferably, the extension member 21 has two leaflet limiters, one on each side of the extension member 21 for each leaflet when the extension member 21 is arranged at the commissures. But, there could also be only one leaflet limiter. This could be the case if it is known that one leaflet is already damaged and moving freely when starting the procedure of measuring and/or deciding the size of the annuloplasty implant. The temporary valve 10 is in an example for short-time replacement, which may be an artificial valve, is positioned inside the native mitral valve 2. In order to facilitate the delivery of the temporary valve 10 and to enable the positioning of the temporary valve 10, the temporary valve 10 may be collapsible for delivery and/or expandable upon delivery. This may be achieved by the use of an at least partly flexible temporary valve 10. The temporary valve 10 comprises an at least partially collapsible and/or at least partially expandable tube. Furthermore, the temporary valve 10 comprises a flange. The flange may be flexible during delivery, and is preferably somewhat rigid once the temporary valve 10 has been implanted. The flange prevents the temporary valve 10 from moving out of position from e.g. the left atrium towards the left ventricle if the valve is for the mitral valve 2 and from moving out of position from e.g. the ascending aorta towards the aortic arc if the valve is for the aortic valve.

The temporary valve 10 is in an example, a one-way valve comprising a tube having an inlet side and an outlet side. The tube may be flexible. This may be advantageous, since the use of the flexible tube prevents interference between the tube and other mitral valve 2 repair devices. Alternatively, the tube may be rigid or at least somewhat rigid. The temporary valve 10 may further comprise a flexible inner sleeve attached to an inlet side of the tube and positioned inside the tube. The flexible inner sleeve may be made of a flexible material such as rubber. The one-way valve works as follows; when the pressure inside the tube is similar to the pressure at the inlet side of the tube, the valve is partly open. Because, the flexible inner sleeve has more or less a same pressure on an inside of the sleeve which is in contact with the inlet side, as on an outside of the flexible inner sleeve which is in contact with the outlet side, thus making the valve partly open. When the pressure inside the tube becomes higher than the pressure at or outside the inlet of the tube, the temporary valve 10 closes. This is because the pressure inside the tube has increased so that the pressure inside the tube, outside of the flexible inner sleeve and in the left ventricle is larger than the pressure at the inlet of the tube, inside of the flexible inner sleeve and the left atrium. When the pressure inside the tube becomes higher than the pressure at and/or outside the inlet of the tube, the valve closes by the flexible inner sleeve contracting together. And, when the pressure inside the tube becomes lower than the pressure at or outside the inlet of the tube, the temporary valve 10 opens. This is because, the pressure inside the tube and outside of the flexible inner sleeve is lower than the pressure at or outside the inlet of the tube and inside of the flexible inner sleeve. When the pressure inside the tube becomes lower than the pressure at or outside the inlet of the tube, the valve and flexible inner sleeve opens. Thus, a simple, yet reliable replacement valve is obtained by the construction of a temporary valve 10 as described above. The one-way valve may further comprise a flange and which may be expandable. In one example, the flange is an expandable balloon.

In an example, the temporary valve 10 is arranged in a substantially centred position of a cross section of the oval cone shape extension member 21. Placing the temporary valve 10 in the centre of the oval cone shape extension member 21 of the commissure location device 20 achieves a very stable construction. Additionally, the flow of the blood through the temporary valve 10 and commissure locator device 20 is maximised. The temporary valve 10 and the commissure locator device 20 are in an example connected at their respective bases to each other. In another example the temporary valve 10 is connected by an outer surface of the temporary valve 10 to an inner surface of the commissure locator device 20.

Figure 3:
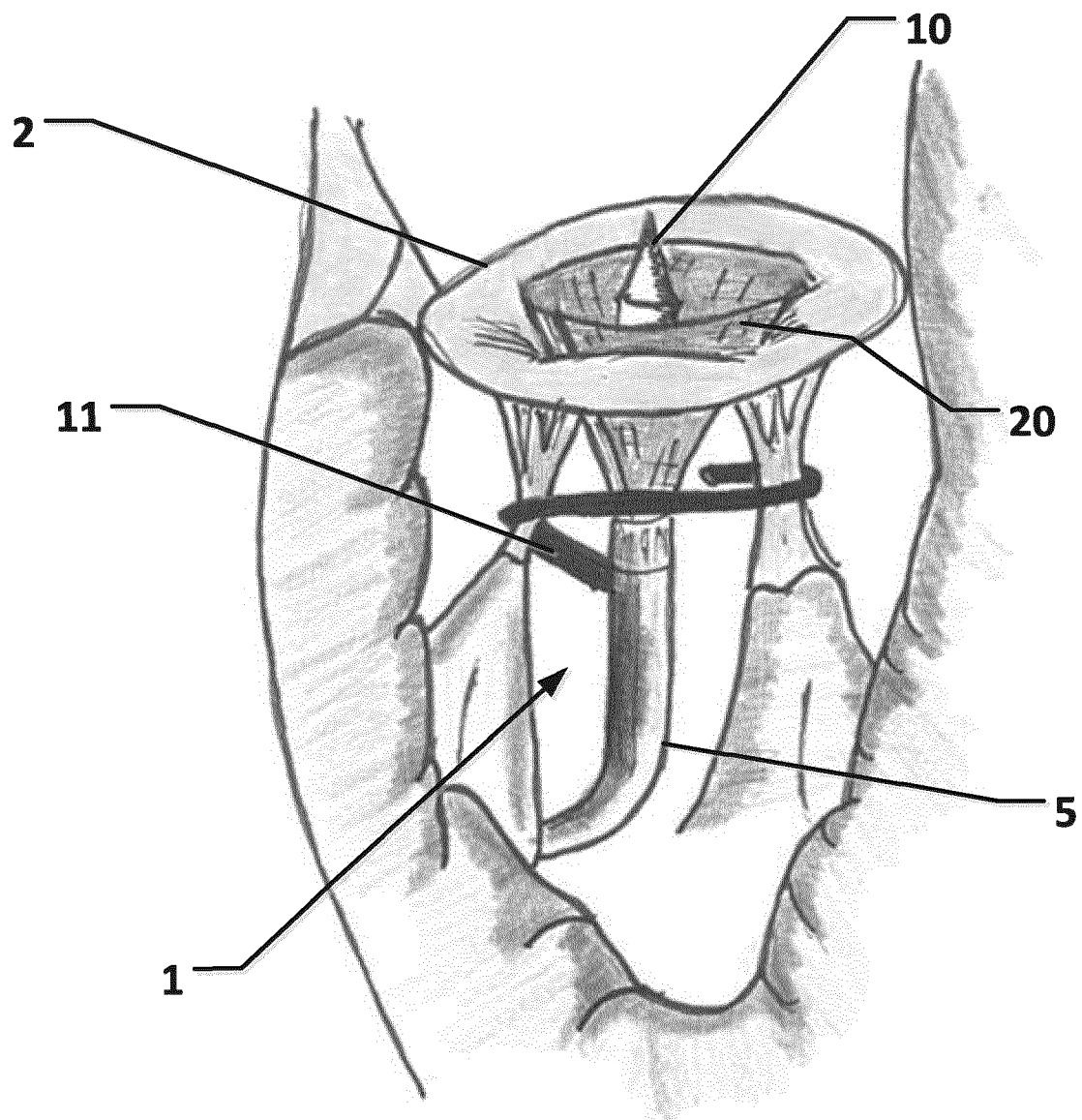
FIG. 3 is a side view of a medical system 1 for repairing a mitral valve.

In another example, illustrated in FIG. 3, the medical system 1 further comprises a chordae collecting unit 11. By using the chordae collecting unit the medical system 1 is further secured in a direction of blood flow to and from the atrium.

In some examples the temporary valve 10 comprises the chordae collecting unit 11 for collecting and arranging chordae towards the temporary valve 10. The temporary valve 10 may be secured, held and/or stabilized in a desired position by the collecting and arranging of chordae towards the temporary valve 10. Thus, a reliable securing of the temporary valve 10 may be achieved.

In an example, wherein a collecting unit 11 is utilized for collecting and arranging chordae towards the valve 10. The collecting unit 11 may together with the tube form one integral part. Alternatively, the collecting unit 11 may be attachable or attached to the tube. In some examples, the collecting unit 11 comprises a single arm or a single hook. Alternatively or in addition, the collecting unit 11 comprises a ring and/or a fluid-filled balloon. A collection unit 11 comprising a fluid-fillable or fluid-filled balloon. The collection unit 11 may in addition to the fluid-fillable or fluid-filled balloon comprise a single arm.

In some examples the valve 10 comprises the collecting unit 11 for collecting and arranging chordae towards the valve 10. The valve may be secured, held and/or stabilized in a desired position by the collecting and arranging of chordae towards the valve 10. Thus, a reliable securing of the valve 10 may be achieved.

By the use of a collecting unit 11, fast and easy replacement of a native valve may be achieved. Furthermore, fast and easy positioning of a temporary valve may be obtained. Therefore, the use of a collecting unit may contribute to give more time to make decisions related to surgery, more time to prepare for surgery and/or more time to perform surgery or medical intervention. Thus, overall quality of valve replacement or repair may be improved. The securing of the valve with chordae together with the shape of the valve 10 and a correct dimensioning of the valve 10 may be advantageous, since a valve with proper dimensions secured by the chordae does not press against any ventricular wall. Thus, there will be no damage to the ventricular walls. Although, there may be a small leakage outside the valve 10, this may be acceptable for a short period of time, such as minutes, hours or a few days.

The valve may thus in certain examples include a collecting unit for collecting and arranging chordae towards the valve. The valve is thus secured, held and/or stabilized in a desired position by the collecting unit and arranging of chordae towards said valve. In an example the collecting unit includes a clip, wherein the chordae and/or leaflets are kept in position towards the valve with said clip. The clip may form a helix. The clip, in particular when in form of a helix, may be integral with or connected to the collecting unit and not a separate piece. Hence, lin some examples, the collecting unit 11 may comprise a clip. The chordae are kept in position towards the valve 10 with the clip. The clip may be formed as a ring or ring-like structure. Alternatively, the clip may be formed or shaped as a helix. Thereby, the clip can easily be rotated into position. Rotation is preferably made together with the valve when the collecting unit, such as a clip, in particular when in form of a helix, is integral with the collecting unit. The chordae and/or leaflets are the kept in position towards the valve with said collecting unit and secured with said clip. This may be advantageous, since a simple and/or fast deployment of the clip is enabled thereby. Furthermore, reliable securing, simple and/or fast deployment of a clip is enabled. Alternatively, when the clip, in particular when in form of a helix, is a separate piece and not integral with or unconnected with the valve, the collecting unit may be rotated separately into position. The clip may then be applied to the collecting unit for securing the latter in position at the chordae and/or leaflets.

In some examples the collecting unit is shaped as a ring or ring-like structure. The ring-shaped unit may be extended to a rod-like structure for delivery and changeable into a ring-like structure upon delivery or implantation. Thus, it may be advantageous to have a collecting unit shaped as a ring, since it may facilitate delivery.

In some examples the collecting unit is a fluid-filled balloon. The fluid-filled balloon may be ring-like The use of a fluid-filled balloon as a collecting unit may be advantageous, since the use of a balloon facilitates delivery and since fluid may be used to stabilize the balloon and/or give some rigidity to the balloon. In one example, the balloon is filled with fluid upon or after delivery at the native valve.

In some examples the collecting unit comprises two hooks or arms. Alternatively, the collecting unit comprises a plurality, such as four, of hooks or arms. The hooks or arms are preferably positioned equidistantly around the valve 10, i.e. the hooks or arms are preferably equidistantly distributed exteriorly along the valve 10.

In some examples, the collecting unit collects and arranges the chordae towards the valve 10 during rotation of the valve 10. The rotation is preferably anticlockwise rotation. The rotation of the valve 10 may be actuated by rotating a catheter, such as a two-axis steerable catheter. Thus, fast and easy collection of chordae may be achieved. Furthermore, fast and easy securing of the valve may be achieved. In addition, with a steerable catheter, fast and easy collection of chordae from outside the body of a patient may be achieved. Moreover, by specifying a direction of rotation, such as clockwise or anticlockwise, a procedure that is less prone to errors, and thus a faster and easier securing of the valve, may be obtained. In addition, reliable securing of the valve 10 and the chordae may be achieved.

In some examples a retracting of chordae with a collection unit comprising a hook, an arm or a wire. A first end of a steerable catheter or wire exits a side lumen of the delivery catheter. The steerable catheter is then moved and manipulated by a user so as to surround the chordae, without touching any ventricular wall. The end of the catheter moves in a radial direction away from the delivery catheter towards the ventricular wall as it is advanced and/or rotated. Once the catheter has encircled all the chordae and 360 degree coverage of the space is achieved, an end unit of the steering catheter or wire is activated to pull the chordae together. Activation may include rotation of the catheter or valve 10 whereupon the curvature of the end of the catheter having grasped the chordae pulls them together towards the valve. The delivery catheter is held stationary during the whole deployment of the steerable catheter or wire.

In another example retracting of chordae with a collection unit comprising two fluid-fillable or fluid-filled balloons. The delivery catheter has two side lumens, which are equidistantly distributed around the delivery catheter, i.e. 180 degrees apart. The two balloon catheters, exits the side lumens of the delivery catheter. The balloon catheters are then manipulated and moved towards a ventricular wall past the chordae. Once the two balloon catheters are in position between the ventricular wall and the chordae, the balloons may be inflated or filled with a fluid. When the balloons have been inflated or filled with a fluid, the balloons will fill the space between the ventricular wall and the chordae and press the chordae away from the ventricular wall and towards the centre and towards each other, i.e. the balloons will encapsulate the chordae and tighten the native valve and bring the chordae towards the delivery catheter. The surfaces of the balloons may be provided with grooves, which form hollow channels when the balloons are fully inflated or fluid-filled. These channels may then guide a ring or a replacement valve during deployment.

In some examples, the medical system comprises a steerable catheter for delivering the artificial valve; an annuloplasty device, which may be used to perform annuloplasty, i.e. to reshape the valve annulus, in order to improve the function of the valve; a location valve expander and/or a clip for locking the chordae in positions towards the artificial valve. This may enable fast and easy replacement of a native valve. Furthermore, it may enable fast and easy positioning of a temporary artificial valve.

In some examples, the catheter enters from the groin and goes via a venous route transseptally to the right atrium for delivery of the valve 10.

The medical system described herein may be utilized for short-term replacement of a native valve and/or for temporary use during beating heart surgery. The device described herein may be utilized for short-term replacement of a native valve and/or for temporary use during beating heart surgery. The valve 10 may be utilized during beating heart surgery. Thus, the system, the device and/or the valve 10 may enable beating heart surgery. Furthermore, the valve may be utilized during life saving intervention, intervention in acute leaflet and/or chordate rupture.

The system, the device and or the valve 10 may provide for a reduced leakage and/or a minimized regurgitation during e.g. beating heart surgery. Furthermore, the system, the device and or the valve 10 may enable precise positioning of an implant or valve 10 in the anatomically correct position. Moreover, the procedure used for delivering a valve 10 described herein enables high accuracy of delivery, positioning and securing of a temporary valve 10.

Therefore, the use of the chordae collecting unit 11 may contribute to give more time to make decisions related to surgery, more time to prepare for surgery and/or more time to perform surgery or medical intervention. Thus, overall quality of the valve repair may be improved. The securing of the temporary valve 10 with chordae together with the commissure locator device 20 may be advantageous, since this does not press against any ventricular wall. Thus, there will be no damage to the ventricular walls.

In some examples, the chordae collecting unit 11 may comprise a clip. The chordae are kept in position towards the temporary valve 10 with the clip. The clip may be formed as a ring or ring-like structure. Alternatively, the clip may be formed or shaped as a helix. Thereby, the clip can easily be rotated into position. This may be advantageous, since a simple and/or fast deployment of the clip is enabled thereby. Furthermore, reliable securing, simple and/or fast deployment of the clip is enabled.

In yet other examples the chordae collecting unit 11 is shaped as a ring or ring-like structure. The ring-shaped unit may be extended to a rod-like structure for delivery and changeable into a ring-like structure upon delivery or implantation. Thus, it may be advantageous to have a chordae collecting unit 11 shaped as a ring, since it may facilitate delivery.

In other examples wherein the temporary valve 10 comprises the chordae collecting unit 11 for collecting and arranging chordae towards the temporary valve 10, the chordae collecting unit 11 is a fluid-filled balloon. The fluid-filled balloon may be ring-like. The use of a fluid-filled balloon as the chordae collecting unit 11 may be advantageous, since the use of the balloon facilitates delivery and since fluid may be used to stabilize the balloon and/or give some rigidity to the balloon. In one example, the balloon is filled with fluid upon or after delivery of the medical system 1 at the native valve.

In another example, the chordae collection unit 11 comprises retracting the chordae with a hook, an arm or a wire. A first end of a steerable catheter or wire exits a side lumen of the delivery catheter 5. The steerable catheter is then moved and manipulated by a user so as to surround the chordae, without touching any ventricular wall. The end of the catheter moves in a radial direction away from the delivery catheter 5 towards the ventricular wall as it is advanced and/or rotated. Once the catheter has encircled all the chordae and an 360 degree coverage of the space is achieved, an end unit of the steering catheter or wire is activated to pull the chordae together. The delivery catheter 5 is held stationary during the whole deployment of the steerable catheter or wire.

In yet another example, the chordae collection unit 11 comprises two fluid-fillable or fluid-filled balloons. The delivery catheter 5 has two side lumens, which are equidistantly distributed around the delivery catheter 5, i.e. 180 degrees apart. The two balloon catheters, exits the side lumens of the delivery catheter 5. The balloon catheters, are then manipulated and moved towards a ventricular wall past the chordae. Once the two balloon catheters are in position between the ventricular wall and the chordae, the balloons may be inflated or filled with a fluid. When the balloons have been inflated or filled with a fluid, the balloons will fill the space between the ventricular wall and the chordae and press the chordae away from the ventricular wall and towards a center of the ventricle and towards each other, i.e. the balloons will encapsulate the chordae and tighten the native valve and bring the chordae towards the delivery catheter 5. The surfaces of the balloons may be provided with grooves, which form hollow channels when the balloons are fully inflated or fluid-filled. These channels may then guide the annuloplasty implant 30 or a replacement valve during deployment.

In some other examples the chordae collecting unit 11 comprises two hooks or arms. Alternatively, the chordae collecting unit comprises a plurality, such as four, of hooks or arms. The hooks or arms are preferably positioned equidistantly around the temporary valve 10, i.e. the hooks or arms are preferably equidistantly distributed exteriorly along the temporary valve 10. In an example of the chordae collection unit the unit comprises two fluid-fillable or fluid-filled balloons. The collection unit may in addition to the fluid-fillable or fluid-filled balloons comprise two arms. Alternatively, the chordae collecting unit comprises a plurality, such as four, of fluid-fillable or fluid-filled balloons. The fluid-fillable or fluid-filled balloons are preferably positioned equidistantly around the temporary valve 10, i.e. the fluid-fillable or fluid-filled balloons are preferably equidistantly distributed exteriorly along the temporary valve 10.

In some examples, the temporary valve 10 comprises a collecting unit for collecting and arranging leaflets towards the temporary valve 10. In these examples, the temporary valve 10 is secured, held and/or stabilized in a desired position by the collecting and arranging of leaflets towards the temporary valve 10. In one example, the temporary valve 10 is secured, held and/or stabilized in a desired position by the collecting and arranging of leaflets towards the temporary valve 10 and by the collecting and arranging of chordae towards the temporary valve 10. In some examples, the valve comprises a collecting unit for collecting and arranging chordae and leaflets towards the temporary valve 10.

Figure 4:
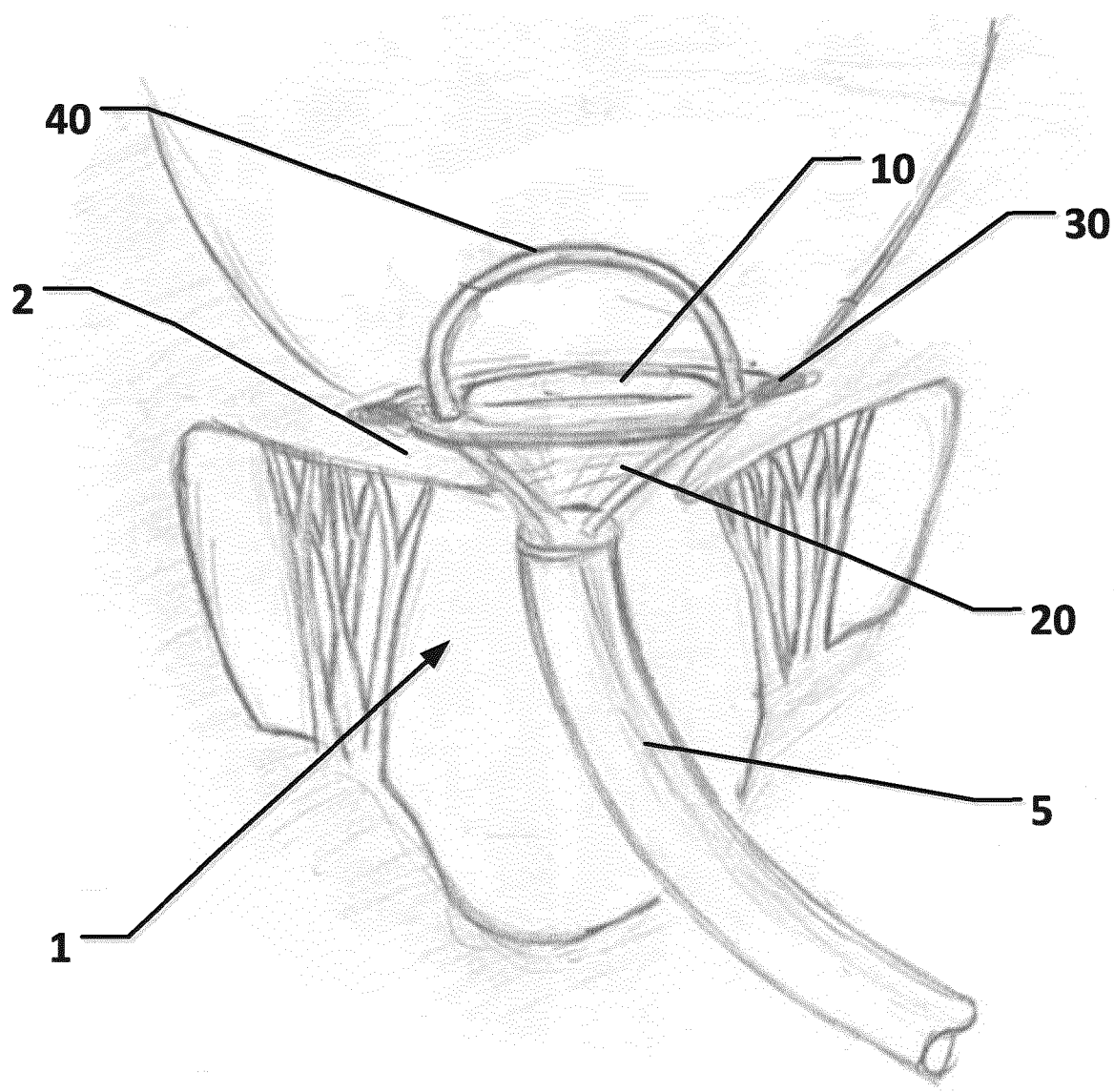
FIG. 4 is a side view of a medical system 1 for repairing a mitral valve.

In an example, illustrated in FIG. 4, the medical system 1 further comprises an atrium support device 40, wherein the atrium support device 40, the temporary valve 10 and the commissure locator device 20 are connected. By having the medical system 1 also comprising the atrium support device 40 it is easier for the surgeon to position and secure the annuloplasty implant 30 since more space is created in the atrium giving the surgeon more freedom to orientate the annuloplasty implant 30. Additionally, the commissure locator device 20 and the temporary valve 10 are even further secured at the mitral valve 2.

In an example, the atrium support device 40 comprises an expandable and contractible intra atrial support member. The support member is resiliently flexible to allow for atrium contraction and expansion, when positioned intra atrial. The support member substantially maintains atrial displacement volume of the beating heart. By using a temporary atrium support device 40 a collapse of the atrium is prevented. The collapse of the atrium could be a consequence of a pressure drop in the atrium introduced by e.g. when performing a repair of a mitral valve 2 and/or other procedures performed in relation with the functioning of the atrium. The atrium support device 40 thus secures the function of the atrium and consequently the heart during a procedure which is related to the atrium and/or the atrium itself, such as the mitral valve 2 repair.

In order to maintain a normal or an adequate function of the atrium the resilient flexibility of the atrium support member results in some examples in an atrium volume that is preferably more than 55 ml, more preferably more than 50 ml, even more preferably more than 20 ml and most preferably more than 15 ml. By having the atrium support member resiliently flexible such that the atrium support member has a volume that may be changed and that never is smaller than a predefined volume, the atrium support member secures that there is a minimum of desired blood present in the atrium and a minimum blood flow is thus ensured. This allows for a beating heart and/or heart support equipment to maintain a minimum circulation of blood in a patient. Further, the resilient flexibility of the atrium support member results in some examples in an atrium volume that is preferably at the most 100 ml, more preferably at the most 90 ml, even more preferably at the most 80 ml and most preferably at the most 60 ml. By allowing the resiliently flexibility of the atrium support member to obtain more than a maximum volume of the atrium the atrium is controlled to result in a maximum atrium volume. Additionally, by defining the flexibility of the atrium support member to the maximum volume the atrium is aided in its reshaping to resume the maximum volume during relaxation of the atrium. Further, by constraining the flexibility of the atrium support member to the maximum volume, damage of the atrium by over-expansion is reduced.

The atrium support member may thus have a predefined maximum expanded cross-section. The atrium support member may thus also have a predefined minimum contracted cross-section when placed in the atrium, such that the compressive force exerted by the atrium on the atrium support member at the minimum contracted cross-section is compensated and counter acted by a reaction force of the support member on the atrium, and where the reaction force is equal to that of said compressive force. The reaction force at the minimum contracted cross-section can thus be set to a pre-defined value. This can e.g. be done during heat setting procedures of the material to define its properties.

The atrium support member is of a shape and material that is capable of being inserted and guided through a catheter 5 to the atrium. The atrium support member is in an example an expandable cage and/or alternatively a wire, an inflatable member comprising at least one channel and/or a covering comprising holes which allows for substantially maintaining the atrial displacement volume. In one example the expandable cage comprises at least two intersecting cage rings, but more preferably more than two intersecting cage rings in order to achieve more area of contact between the cage rings outer surface towards the atrium tissue and the atrium tissue. The atrium support member may comprise an inlet and outlet for blood flow. This assures that the natural flow of blood is not disturbed while maintaining the displacement volume.

In another example the at least one channel in the inflatable member comprises a valve. The valve may be of the cardiac valve type, i.e. being closed when the heart chamber ejects blood to the body or lungs respectively and open during a refill phase. The dimension of the at least one channel and any possible valve is chosen based on a wanted atrial displacement. The same applies for selection of the size of the holes in the covering.

The expansion of the atrium support member may be performed in a variety of ways and the atrium support device 40 may be comprised of a wide selection of materials capable of being temporary introduced into the atrium and being expandable from the catheter 5 without diverging from the scope of the invention. Following, some examples will be giving but they should not be construed as limiting.

The atrium support member is preferably made of a material that is biocompatible and designed in such way that the atrium support member does not induce any damages to the catheter 5 and/or the atrium.

For example the atrium support device 40 comprises a memory shape material, wherein the memory shape material has a first shape when deployed and a second expanded shape activated by a shape memory temperature. By using the atrium support device 40 comprising the shape memory material it is possible to activate the atrium support device 40 to expand to the second expanded shape in a controlled and faster way than with other expansion techniques. Further, the memory shape material allows for better customising the expanded shape of the atrium support device 40 to better suit the shape of the atrium. Suitable materials for the shape memory material are e.g. copper-aluminium-nickel alloys, nickel-titanium alloys and/or other known shape memory materials.

In yet another example the atrium support member comprises a heat set shape, and wherein the atrium support member 101 elastically returns to the heat set shape. By use of the heat set shape it is possible to get an atrium support member which has inherent elastic properties to a desired shape and can easily be deployed trough the catheter 5. Suitable materials for the heat set shape are e.g. nickel-titanium alloys and/or other known heat set shape materials.

In another example, the atrium support device 100 comprises and/or acts as, a leaflet limiter which limits abnormal movement, such as prolapse, of the leaflets into the atrium. Such abnormal movement may arise if a chordae, or several chordae, that usually limits the movement of the leaflet is completely destroyed and the leaflet may thus freely move in the left atrium and/or left chamber. The leaflet limiter is made of a material that can expand together with the atrium support device 100, and/or it may be made of the same material as the atrium support device 100. Alternatively, the leaflet limiter is expanded by a spring back when exited from the catheter 50. The leaflet limiter may be a crossbar that extends and is projected laterally from the atrium support device 100. The number of leaflet limiters and their placement is chosen based on the circumstance that the atrium support device 100 is used in and may thus be of a number of different shapes and have various placements. One example would be to have a simple projection outwards towards the leaflets from the atrium support device 100 that limits the movement or other suitable shapes that limits but not damage the leaflet(s) when hindering its movement into the atrium. Preferably, the atrium support device 100 has two leaflet limiters, one on each side of the atrium support device 100 for each leaflet. But, there could also be only one leaflet limiter if it is known that one leaflet is already damaged and moving freely when starting a procedure of deploying the atrium support device 100. As mentioned, the atrium support device itself may acts as a leaflet limiter when expanded in the atrium, and no other component may be required. This provides for a device that limits leaflet movement that is easy to handle and position.

In an example the atrium support device 40 comprises means for aligning the atrium support device 40 by use of at least one commissure, wherein the means for aligning comprises a first end and a second end, and wherein the first end of the means for aligning is connected to the atrium support member and the second end is directed outwards from the atrium support member towards the at least one commissure. The means for aligning the atrium support member assists in aligning and securing the atrium support member from rotation when the atrium is e.g. relaxed with a larger volume than the atrium support member and/or the atrium support member comprises the inflatable member with the at least one channel. In one example, if the atrium is relaxed with the larger volume than the atrium support member the means for aligning is for securing and aligning the atrium support member to the atrium so that the atrium support member remains substantially at the same location during the expansion and contraction of the heart and no unnecessary damages occurs due to any rotation and/or twisting of the atrium support member. In another example, if the atrium support member comprises the inflatable member with at least one channel which extends from the pulmonary vein to the mitral valve 2, the means for anchoring ensures that the atrium support member aligns the channel to the pulmonary vein and the mitral valve 2 during the expansion and contraction of the atrium so that blood flow is secured between the pulmonary vein and the mitral valve 2.

The means for aligning the atrium support member is in one example a pair of projections, projecting outwards from the atrium support member. By using a pair of projections for aligning the atrium support member, a simple but yet effective alignment of the device is achieved. For example the atrium support member is easily aligned by simply using the pair of projections at and/or into suitable aligning sites in the atrium such as the commissures and/or the mitral valve 2 and the pulmonary vein.

In some examples the atrium support member is partly in contact with the atrium. By allowing the atrium support device 40 being partly in contact with the atrium the support device is e.g. chosen to support a larger section of the atrium or chosen to support a smaller section of the atrium. Alternatively, the atrium support member is in contact with substantially the entire atrium. By having the support device contacting the entire atrium, maximum support and prevention of collapse of the atrium is ensured.

The atrium support member may be designed in a variety of ways to provide partial contact or substantially full contact or get into apposition with the atrium. Such designs are e.g. the atrium support member is bent when expanded, such as banana shaped. The atrium support member may be spherical when expanded. The atrium support member may be bulb shaped when expanded. Alternatively, the atrium support device 40 comprises a plurality of atrium support member. By use of a plurality of atrium support members it is possible to customise the overall shape and size of the atrium support device 40 to better adapt to the shape of the atrium than a single atrium support member. Further, it would be possible to have atrium support members with different flexibility at different locations in the atrium which allows for better compliance of the atrium support device 40 with the expansion and contraction of the atrium during beating of the heart.

In yet another example, the atrium support device 40 further comprises means for guiding the annuloplasty implant 30 from an insertion site to a securing site at a heart valve. By having the atrium support device 40 further comprising guiding means it is possible to aid the operator to in deploying the annuloplasty implant 30 to the heart valve. This allows for faster attachment of the annuloplasty implant 30 compared to when the operator need to introduce other equipment to secure the annuloplasty implant 30.

In one example the guiding means of the atrium support device 40 is at least one ring shaped member arranged at an outer surface of the atrium support member. The use of at least one ring shaped member provides a simple yet effective solution for guiding the annuloplasty implant 30 into place. The outer surface of the atrium support member is the surface facing the tissue of the atrium. The arrangement of the at least one ring shaped member on the outer surface of the atrium support member is achieved by e.g. attaching the ring shaped member at, on or through the outer surface.

In another example the means for guiding is a channel arranged along an outer surface of the atrium support member. The use of the channel as the guiding means is particularly beneficial when the atrium support member is a sheet, covering or other shell shaped atrium support member. In such case the annuloplasty implant 30 is guided along the channel arranged along the outer surface of the atrium support device 40 to a desired heart site. The channel is preferably a coherent channel but may also be a sectioned channel.

In yet another example the means for guiding is a plurality of holes at the atrium support member. The use of holes in the atrium support member the guiding of the annuloplasty implant 30 is performed through the atrium support member which allows for the atrium support member to protect the tissue and/or other parts of the atrium when positioning the annuloplasty implant 30. Additionally, the use of the plurality of holes provides guiding when the annuloplasty implant 30 has a smaller diameter than the atrium support member and a minimum of strain is to be exerted to the annuloplasty implant 30.

Yet an alternative example, the atrium support member comprises e.g. the inflatable member or another substantially solid object, the means for guiding is at least one channel arranged through the atrium support member. The use of at least one channel through the atrium support member provides the same solution for protecting the atrium and exerting the minimum of strain as with the plurality of holes. In addition, the at least one channel through the atrium support member ensures for a more accurate and simple guiding of the annuloplasty implant 30 to the desired heart site.

Figure 5:
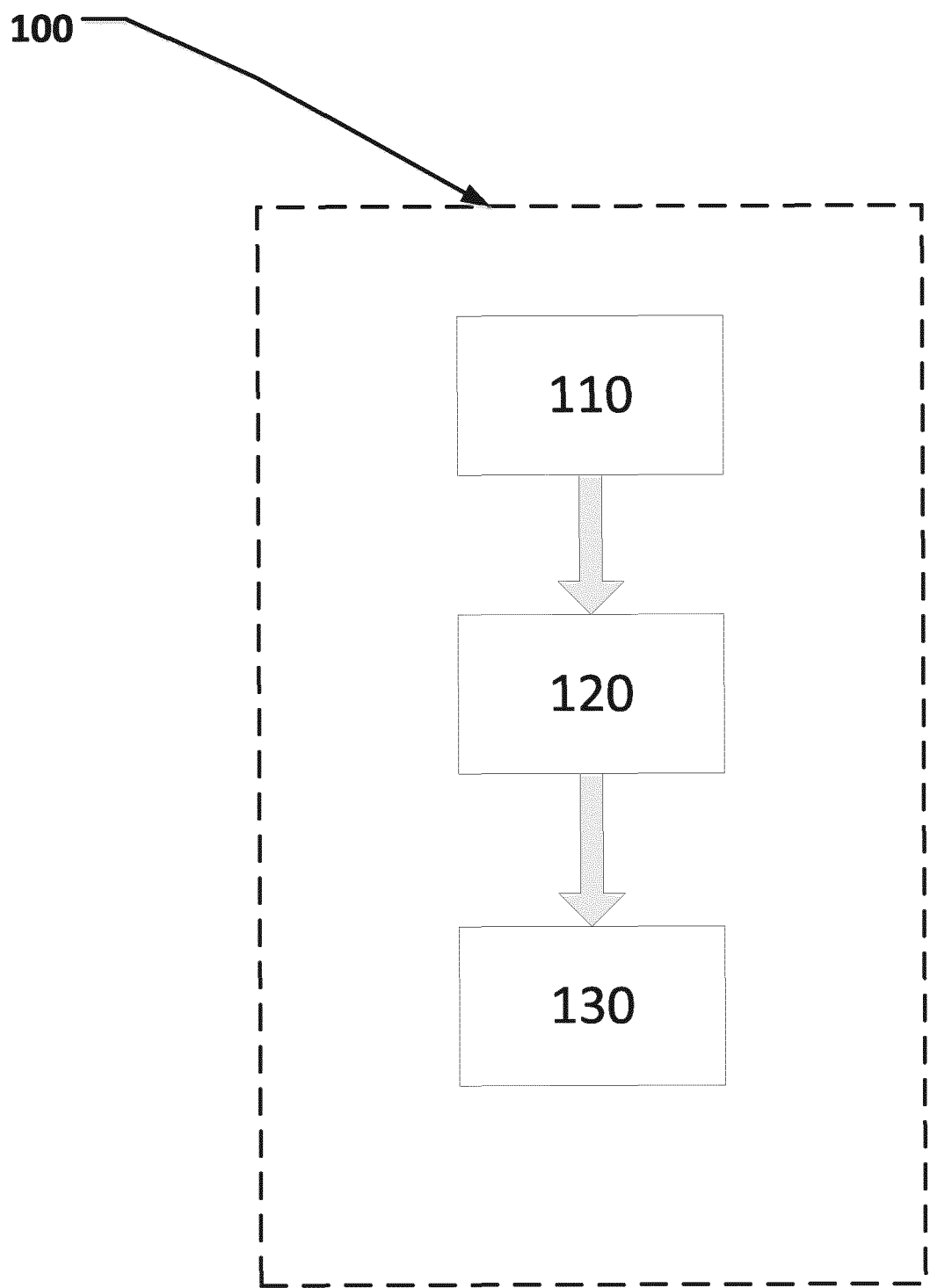
FIG. 5 is a flow chart of a method for repairing a mitral valve.

An example of a method 100 is illustrated in FIG. 5 for repairing a mitral valve 2 comprising the steps of in one manoeuvre 110, positioning a temporary valve 10 by use of a commissure locator device 20 connected to the temporary valve 10 and measuring a size and/or a shape of an annuloplasty implant 30 by use of the commissure locator device 20. The method further comprises positioning 120 the annuloplasty implant 30 at the mitral valve 2, and securing 130 the annuloplasty implant 30 at the mitral valve 2 for repairing the mitral valve 2. By using the method 100 described above it is possible to quickly and easily repair a valve defect, such as regurgitation.

In an example the step 110 comprises positioning, preferably minimally invasively, the distal end of the catheter 5 at the mitral valve 2 of a patient. The method further comprises extending the measurement end of the extension member 21 relative from the distal end of the catheter 5, bringing the measurement end in apposition with at least one commissure of the cardiac valve, such as the mitral valve 2 of the patient. The annuloplasty implant's 30 shape and/or size is based on at least an extended length of the extension member 21 relative from the distal end of the catheter 5 to the at least one commissure. By using the commissure locator device 20 for facilitating the selection of the shape and/or size of the annuloplasty implant 30 comprising the catheter 5 and the extension member 21 it is possible to base the size/and or shape of the annuloplasty implant 30 on the extension of the extension member 21 relative from the catheter 5.

In one example, the catheter 5 is positioned in a substantially centre position at the cardiac valves. Following the extension member 21 is extended from the distal end of the catheter 5 by an operator pushing the extension member 21 from the proximal end of the catheter 5 through the catheter 5 and out at the distal end of the catheter 5. The measurement end of the extended extension member 21 is positioned at, appositioned, or in contact with the commissure.

The positioning of the extension member 21 is performed in a number of ways such as by rotating the extension member 21 relative to the catheter 5, sliding the extension member 21 inside the catheter 5, by synchronised movement of the catheter 5 and the extension member 21 and/or by synchronised movement of the catheter 5 and the extension member 21 where the extension member 21 and the catheter 5 is engaged so that when movement of the catheter 5 is performed the extension member 21 is moved in the same way as the catheter 5.

The extended length of the extension member 21 from the substantially centre position to the commissure gives the operator a measure on the size and/or shape of the annuloplasty implant 30. The extended length is in one example used as basis for the radius of the annuloplasty implant 30. In another example an assumption that the cardiac valve is symmetrical together with the extended length of the extension member 21 is used as basis for the width of the annuloplasty implant 30.

In another example of the method for facilitating selection of a shape and/or size of an annuloplasty implant 30 the basing of the annuloplasty implant 30's shape and/or size is based on a measured valve width between two commissures of the mitral valve 2 by the extension of the measurement end of the extension member 21 relative from the catheter 5 to the two commissures. Basing the selection of the annuloplasty implant 30 on the distance between the two commissures gives a better fit of the annuloplasty implant 30 than when only using one commissure. In one example the width between the two commissures are measured by sweeping the extension member 21 from one commissure to the other commissure.

In another example the width is obtained between the two commissures by arranging of two separable sections of the extension member 21 separable towards the commissures. The use of the extension member 21 comprising two separable sections separable towards the commissures results in the width between the commissures being measured more accurately and faster than any presently known method. When obtaining the width between the commissures by use of the extension member 21 comprising two separable sections the operator positions the catheter 5 at the cardiac valve and extends the extension member 21. The two separable sections separate outwards towards the commissures when they passes the distal end of the catheter 5 by the operator pushing the extension member 21 through the catheter 5 from the proximal end of the catheter 5. Depending on the pushed distance of the extension member 21 i.e. extended distance of the extension member 21 and the two separable sections the width of the commissures is known. The separation of the two separable sections is preferably at a predefined angle and/or settles at the predefined angle when measuring the width between the commissures. The extension of the extension member 21 from the catheter 5 may be performed in several ways such as, out from the proximal end of the catheter 5 and/or out through the sidewall of the catheter 5 at the proximal end.

In one example the method further comprises measuring an applied manoeuvre force on the extension member 21 while maneuvering the extension member 21 to apposition the measurement end with the at least one commissure and, indicating when the measurement end is apposition with the at least one commissure based on the measured applied manoeuvre force. By measuring the applied manoeuvre force on the extension member 21 applied by the operator the indication of when at least one commissure has been found is performed more reliable than by use of tactile indication through the extension member 21. The measurement of the applied manoeuvre force may e.g. be measured by a force detection unit.

In one example if the force detection unit is used, the force detection unit bases the indication of the apposition to the at least one commissure by comparing the measured applied manoeuvre force with a predefined commissure value for triggering the indication of the apposition of the measurement end with the at least one commissure.

In another example of the method for facilitating selection of a shape and/or size of an annuloplasty implant 30 an indication is based on a measured force for stretching the extension member 21 between two commissures. By measuring the force needed to extend and/or stretch the extension member 21 outwards towards the two commissures it is possible to detect when the two commissures have been found since the two commissures have a difference in flexibility compared to other tissue in the atrium.

In yet another example the method comprises anchoring at least one anchor at at least one commissure by use of the extension member 21 comprising anchoring means. By using at least one anchor at at least one commissure by using the extension member 21 the operator can attach anchors for the annulopasty device in one go and with the same device, saving time compared to needed to use a second instrument for attaching anchors.

The above described ways of positioning the commissure locator device 20 comprising the extension member 21 and wherein measuring the size and/or shape of the annuloplasty implant 30 at the same time is also applicable to the temporary valve 10 to since the commissure locator device 20 and the temporary valve 10 is connected so when the commissure locator device 20 is positioned the temporary valve 10 is also positioned.

To further clarify, in one example the step of position the temporary valve 10 is performed by the catheter 5 being utilized for delivering the temporary valve 10 for short time replacement of a native valve, such as the mitral valve 2, and the connected commissure locator device 20.

Once the catheter 5 has entered the left ventricle, the catheter 5 is forwarded so that it is at least partly put through the mitral valve 2 and partly into the left atrium. Thereafter, the temporary valve 10 connected to the commissure locator device 20 is deployed from the end of the delivery catheter 5. In order to facilitate the delivery of the temporary valve 10 and the commissure locator device 20, they are collapsible for delivery and/or expandable upon delivery. The temporary valve 10 is connected at the centre of the commissure locator device 20 so when expanded for positioning and measuring 110 the temporary valve 10 is expanded centrally of and interior of the commissure locator device 20 allowing the commissure locator device 20 to be positioned by using the commissures. This deployment secures the function of the temporary valve 10 and the commissure locator device 20 and results in that when the commissure locator device 20 is positioned, so is the temporary valve 10.

In another example the positioning and measuring 110 is performed by moving the temporary valve 10 and the commissure locator device 20 downwards from the atrium towards the ventricle. This allows for the surgeon to wedge the commissure locator device 20 and the temporary valve 10 into position at the mitral valve 2. The commissure locator device 20 may thus be expanded, together with the temporary valve 10, to have a greater width and/or area than the mitral valve 2 inside the atrium. When moved downwards the commissure locator device 20 will be positioned by itself, if using e.g. the oval cone shaped extension member 21, thus making the alignment with the mitral valve 2 easy.

In an example, the temporary valve 10 and the commissure locator device 20 is further secured by use of a chordae collecting unit 11 connected to the temporary valve 10 and the commissure locating device 20. Further securing the temporary valve 10 by using the chordae collecting unit 11 secures the temporary valve 10 and the commissure locator device 20 in a flow direction of the blood to and from the atrium in a better way than previously.

For example, once the temporary valve 10 has been positioned inside the native valve, a plurality of chordae may be pulled together and towards the temporary valve 10 for fixation of the valve 10 by the chordae collecting unit 11.

Pulling of a plurality of chordae together is in some examples performed for creation of a temporary space between at least one chorda and the ventricular wall of the heart. Within this temporary space, the annuloplasty implant 30 may pass for delivery. Thus, an additional space may be created between e.g. at least two chordae and the ventricular wall of the heart by pulling a plurality of chordae together. Through the additional space an annuloplasty implant 30 may be advanced into position. The insertion of an annuloplasty implant 30 is preferably performed after the valve 10 has been positioned.

The plurality of chordae may in some examples be pulled together by rotation or twisting of the valve 10. The rotation of the valve 10 for pulling the chordae together is preferably specified to one direction, such as anticlockwise rotation. The rotation of the valve 10 may be actuated by rotating the catheter 5. As an example, a two-axis steerable catheter 5 may be used for actuating the rotation of the valve 10.

A clip may thereafter be deployed to surround the valve 10 and/or to keep the chordae in position towards the valve 10. In some examples, the clip is deployed by pushing it out of the catheter 5 and into position with a pusher or a pushing catheter. Alternatively or in addition, the clip may be delivered with a special clip guide tube. The catheter 5 may thereafter be removed or utilized for inserting further implants or devices, such as the annuloplasty implant 30.

In another example, the step of positioning of the temporary valve 10 and the commissure locator device 20 further comprises by use of an atrium support device 40 connected to the commissure locator device 20 and the temporary valve 10. By also using the atrium support device 40 for positioning the medical system 1, the medical system 1 is further secured and at the same time there is created more space in the atrium for deployment of the annuloplasty implant 30.

The atrium support member 40 is connected to the commissure locator device 20 and the temporary valve 10 so that when the commissure locator device 20 and the temporary valve 10 is expanded from the catheter 5 the atrium support member 40 is expanded together with them and on top of them in the atrium. The atrium support member 40 is in an example expanded to more or less contact all of the atrium so that the medical system 1 can not move in the direction of the blood flow between the atrium and the ventricle.

The expansion of the atrium support device 40 intra-atrial preventing the collapse of the atrium is performed by use of a force on the atrium support device 40. Such force may be a pulling force, a pushing force, an elastic force and/or an expansion force.

In another example the expansion of the atrium support device 40 is performed by use of applying a shape memory temperature to the atrium support device 40. By using the shape memory temperature to the atrium support device 40 the atrium support device 40 is triggered to expand. The shape memory temperature is chosen to be triggered at e.g. a temperature of the blood in the atrium or a temperature of a heating element.

In yet another example the expansion of the atrium support device 40 is performed by use of supplying a gas or liquid to the atrium support device 40. The use of the liquid for expanding the atrium support device 40 allows for water or blood to inflate the atrium support device 40 comprising an inflatable member reducing any complications if a leak of the atrium support device 40 would occur. If using gas to inflate the atrium support device 40 comprising the inflatable member the atrium support device 40 is inflated by using accessible means during heart surgery.

Within this disclosure the term short-time or short-time replacement has been used. Short-term replacement and/or repair of native valves is considered to be a temporary replacement. Such a temporary replacement may be a replacement that last for minutes, hours or possibly up to a few days. Short-term replacement includes non-indwelling, i.e. non-permanently implanted, devices and methods described herein. Short-term replacement devices are intended to be removed from the body after use. With a long-time replacement is herein meant a replacement, which last for several days, weeks, months or longer. Such a long-time replacement may be made with devices intended to be permanently implanted and not removed from the body, such as indwelling annuloplasty devices. Structural requirements for such devices are thus different for short-term use and long-term use.

While several examples of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A medical system for repairing a mitral valve comprising:
   a temporary valve,
   a commissure locator device for locating at least one commissure,
   said commissure locator device and said temporary valve being connected,
   said temporary valve being connected at the center of the commissure locator device, whereby when the commissure locator device is expanded for positioning, the temporary valve is expanded centrally of, and interior of, the commissure locator device;
   a clip guide tube;
   a helix-shaped clip being deliverable from said clip guide tube to surround said temporary valve and arrange chordae towards the temporary valve to keep the position of the chordae towards the temporary valve.

2. The medical system according to claim 1, further comprising an annuloplasty implant, wherein said annuloplasty implant has a helix shape.

3. The medical system according to claim 1, wherein said commissure locator device is adapted for locating at two opposite commissures.

4. The medical system according to claim 1, further comprising an atrium support member, wherein the atrium support member, the temporary valve and the commissure locator device are connected.

5. The medical system according to claim 1, wherein the commissure locator device comprises an extension member, and wherein said extension member is at least partly arranged inside a catheter.

6. The medical system of claim 5, comprising said catheter, said catheter having an operator end and a distal end, and said extension member having a measurement end that is extendable relative from the distal end of the catheter for apposition with said at least one commissure.

7. The medical system of claim 6, wherein the commissure locator device is adapted to provide a measure for a shape and/or size of an annuloplasty implant for repairing said mitral valve, wherein the measure related to a selection of the annuloplasty implants shape and/or size is based on at least an extended length of the measurement end of the extension member from the distal end of the catheter, when positioned at the cardiac valve, to the at least one commissure.

8. A method for repairing a mitral valve comprising the steps of:
   in one maneuver, positioning a temporary valve by use of a commissure locator device connected to the temporary valve, wherein the temporary valve is connected at the center of the commissure locator device, whereby when the commissure locator device is expanded for positioning a portion of said commissure locator device is in apposition to at least one commissure of said mitral valve and the temporary valve is expanded centrally of, and interior of, the commissure locator device, the method further comprising
   delivering a helix-shaped clip from a clip guide tube to surround the temporary valve and to arrange chordae towards the temporary valve to keep the position of the chordae towards the temporary valve,
   measuring a size and/or a shape of an annuloplasty implant by use of the commissure locator device,
   positioning the annuloplasty implant at the mitral valve, and
   securing the annuloplasty implant at the mitral valve for repairing the mitral valve.

9. The method according to claim 8, wherein the step of positioning the temporary valve and the commissure locator device is performed by moving the temporary valve and the commissure locator device downwards from the atrium towards the ventricle.

10. The method according to claim 8, where access to the mitral valve is gained transfemoral or transapical.

* * * * *